US00PP15165P2

(12) United States Plant Patent
Olesen et al.

(10) Patent No.: US PP15,165 P2
(45) Date of Patent: Sep. 21, 2004

(54) CLEMATIS PLANT NAMED 'EVIPO025'

(50) Latin Name: *Clematis viticella*
Varietal Denomination: EVIpo025

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 11 days.

(21) Appl. No.: 10/640,802

(22) Filed: Aug. 13, 2003

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new Clematis cultivar which is well suited to propagation in glasshouses. With a tall growth habit, profuse, purple flowers, and continuous summer flowering. The variety successfully propagates from softwood cuttings and is suitable for cultivation in commercial glasshouses. This new and distinct variety has shown to be uniform and stable in the resulting generations from propagation.

1 Drawing Sheet

Botanical classification: *Clematis viticella.*
Variety denomination: 'EVIpo025'.

SUMMARY OF THE INVENTION

The present invention constitutes a new and distinct variety of Clematis which originated from a controlled crossing between Clematis 'Burma Star', non-patented, and Clematis 'Royal Velvet' EVIfour, described in U.S. Plant Pat. No. 9,299 issued Oct. 28, 1994. The two parents were crossed and the resulting seed was planted in a controlled environment.

The new clematis may be distinguished from its male pollen parent, Clematis 'Burma Star', by the following combination of characteristics:

1. Average range of height for Clematis 'Burma Star' is 2 to 2.5 meters, while that of 'EVIpo025' is typically 1.5 to 2 meters.
2. Tepals of Clematis 'Burma Star' are typically Red-Purple Group 72, tepals of 'EVIpo025' are Violet Group 86.

The objective of the hybridization of this Clematis variety for commercial glasshouse and nursery culture was to create a new and distinct variety with unique qualities that this variety has:

1. Purple flowers.
2. Very free flowering.
3. Good repeat flowering.
4. Flowers well as a young plant.
5. Compact habit.
6. Good choice for small container use.

These qualities required improvement in Clematis varieties that were in commercial cultivation and the objectives have been substantially achieved in the new variety, as evidenced by the unique combination of characteristics that are present in 'EVIpo025' which distinguish it from all other varieties of which we are aware.

The seeds from the aforementioned hybridization were germinated and evaluations of the resulting seedling plants were conducted in a controlled environment. As a result, 'EVIpo025' was selected by Raymond J. Evison and Mogens N. Olesen in their Clematis development program in Domarie Vineries Les Sauvagees, St. Sampsons, Guernsey, Channel Islands, United Kingdom in 1998.

Asexual reproduction of 'EVIpo025' by cuttings was first done by Raymond J. Evison and Mogens N. Olesen in Domarie Vineries Les Sauvagees, St. Sampsons, Guernsey, Channel Islands, United Kingdom in 1998. This initial and subsequent propagations have demonstrated that the characteristics of 'EVIpo025' are true to type and are transmitted from one generation to the next.

BRIEF DESCRIPTION OF THE DRAWING

The accompanying color illustration show as true as is reasonably possible to obtain in color photographs of this type:

FIG. 1.1 Juvenile stem with petioles and attachment of flower bud;

FIG. 1.2 Mature compound leaf and leaflets;

FIG. 1.3 Flower bud and partially opened flower;

FIG. 1.4 Open flower, upper side;

FIG. 1.5 Open flower, lower side.

DETAILED DESCRIPTION OF THE VARIETY

The following is a detailed description of 'EVIpo025', as observed in its growth throughout the flowering period in 2 liter pots in an unheated glasshouse at Domarie Vineries Les Sauvagees, St. Sampsons, Guernsey, Channel Islands, United Kingdom. Observed plants are 2 years of age. Certain phenotypical characteristics of the variety may vary under different environmental, cultural, agronomic, seasonal, and climatic conditions. Color reference are made using The Royal Horticultural Society (London, England) Colour Chart, 2001.

For a comparison, the nearest existing Clematis variety is Clematis 'Royal Velvet' EVIfour, a patented variety described and illustrated in U.S. Plant Pat. No. 9,299 and issued on Oct. 28, 1994. Chart 1 details several physical characteristics of 'EVIpo025' and the comparison variety.

CHART 1

| | 'Evipo025' | 'Evifour' |
|---|---|---|
| Growth | Compact: seasons growth normally 1.5 m–2.0 m. Internode length is 60 mm–80 mm. | Average: seasons growth normally greater than 2.0 m. internode length 120 mm–160 mm. |
| Flower size | Small 100–130 mm diameter. | Medium 120–160 mm diameter. |
| Ability to flower | Improved flowering as a young plant | |
| Tepal arrangement | Tepals overlap giving very "full" flower appearance. | Tepals only touch or overlap slightly. |

Parents:
*Pollen parent.*—'Burma Star'.
*Seed parent.*—'EVIfour'.

FLOWER AND FLOWER BUD

Blooming habit: May through September.
Flower bud:
*Size.*—20 to 30 mm in length. Bud diameter is 12 to 15 mm.
*Bud form.*—Ovate.
*Bud color.*—RHS 138D of the Green Color Group at ¼ open.
*Tepals.*—RHS 86A of the Violet Color Group.
Peduncle:
*Surface.*—Smooth.
*Length.*—40 mm to 60 mm average length.
*Color.*—RHS 60 A of the Red-Purple Color Group.
*Strength.*—Erect.
Receptacle: None.
*Borne.*—In clusters. Compound cymes. Some early seasons flowers may be borne singly.
Flower bloom:
*Size.*—Medium. 100 to 130 mm in diameter. Flower depth is 5 to 10 mm. Anthers and stigmas protrude an additional 10 mm.
*Form.*—Upon opening, flat to concave, with tepals normally straight, occasionally reflexing.
*Color.*—Upon opening: Upper surface of tepals is RHS 86A of the Violet Color Group. Lower surface is RHS N79D of the Purple color group. There is a central bar, the color of Green Group 138C surrounded by white Group 155B. After opening: Upper surface is RHS 86A of the Violet color group. Basal zone is Violet Group 86A. Lower surface is RHS N79D of the Purple Color Group. There is a central bar, the color of Green Group 138C surrounded by white Group 155B.
*Variations.*—The upper surface of the tepal has a slight central bar that becomes more evident as the flower ages. Color Purple N79C.
*Lastingness.*—Flowers persist 7 to 12 days on the plant.
*Fragrance.*—None.
Tepals:
*Size.*—Length 50 to 60 mm. Width 25 to 30 mm.
*Tepal count.*—Double. Average range is 6 to 8 tepals.
*Shape.*—Individual tepal shape is elliptic.
*Cross section.*—Flat.
*Undulation of margin.*—Weak.
*Margins.*—Entire.
*Tepal apex.*—Narrowly acute.
*Tepal base.*—Rounded.
*Recurvature of tip.*—Outer sepals occasionally recurved.
*Persistence.*—Tepals fall from plant cleanly.
*Arrangement.*—Tepals are arranged regularly.
Reproductive organs:
*Pollen.*—Color: Yellow Group 2D.
*Anthers.*—Size: 7 to 12 mm in length. Color: Red-Purple Group 71A.
*Filaments.*—Size: 5 to 10 mm. Color: Red-Purple Group 61A.
*Pistils.*—Quantity: 35 to 45.
*Stigmas.*—As the flower ages the stigma may protrude slightly from between the anthers. Color: Yellow Group 2D.

PLANT

Plant form: Climbing and spreading.
Plant growth: Average vigor.
Height: Seasons growth attains 1.5 to 2.0 meters.
Spread: 0.5 to 1.0 meter.
Hardiness: Trials to date show the variety hardy in USDA Zones 4–9.
Stems:
*Color.*—Older wood: Greyed-Orange Group 165C.
*Internodes.*—Shape: Cylindrical. Length: 60 to 80 mm.
*Petioles.*—Size: Average length is 30 to 60 mm. Petioloule is 15 to 30 mm. Color: Red, nearest RHS designation is Greyed-Purple group 187A. Clasping: By winding leaf petiole.
*Bark.*—Young wood: Smooth. Older wood: Smooth.
*Stem size.*—Length is 100 to 150 cm. Diameter is 2 mm.
Plant foliage:
*Leaf characteristics.*—Deciduous. 3 ovate leaflets arranged in pinnate from.
*Compound leaf.*—180 mm (l)×100 mm (w).
*Color.*—Top: Dark green. RHS 137A of the Green Color group. Bottom: Medium. RHS 137B of the Green Color group. New Growth: Green RHS 137C.
Plant leaves and leaflets:
*Stipules.*—Absent.
*Petioles.*—Length is 30 to 60 mm. Underneath: Without prickles.
*Leaf edge.*—Terminal leaflet margin is entire.
*Shape.*—Base of leaflet: Acute and rounded. Apex of leaflet: Acute.
*Texture.*—Upper side: Glabrous. Lower side: Ribbed.
*Thickness.*—Thin.
*Glossiness.*—Matte.
*Leaflet size.*—50 to 70 mm in length by 30 to 40 mm wide.
Disease resistance: Subject to any disease that normally attacks the species, however the variety is more tolerant to botrytis than some Clematis.

We claim:

1. A new and distinct variety of Clematis plant named 'EVIpo025', as illustrated and described herein as a distinct and novel clematis variety due to its abundant purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

EVIpo025
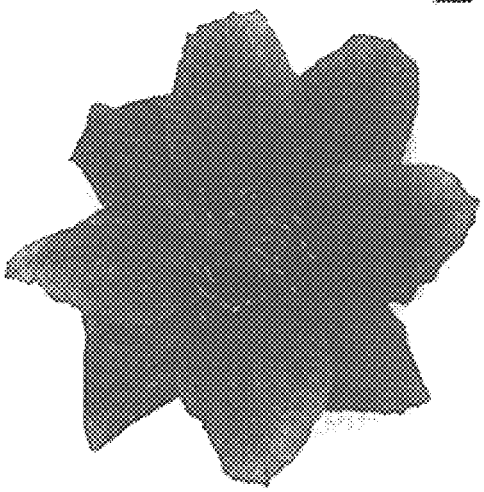
Fig. 1.4
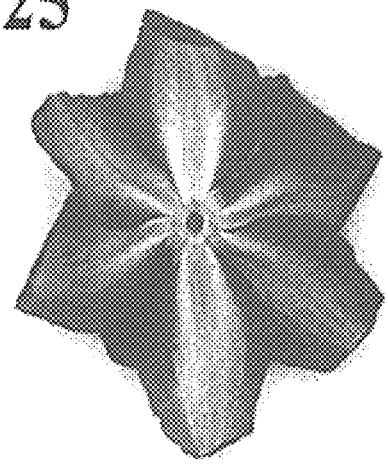
Fig. 1.5
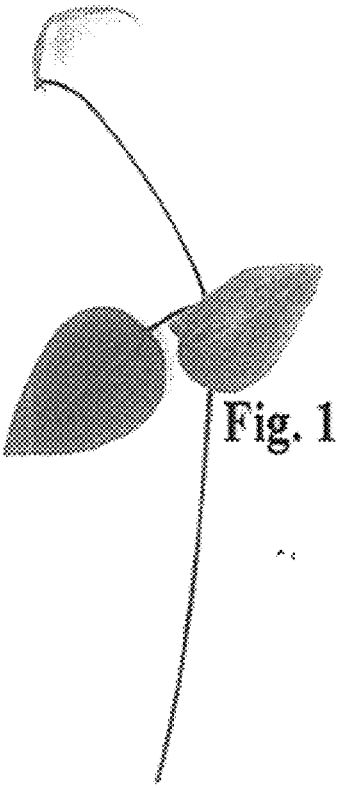
Fig. 1.2
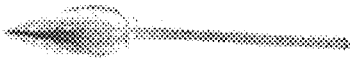
Fig. 1.3
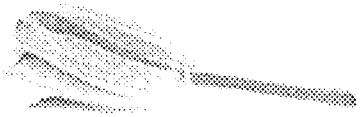
Fig. 1.1
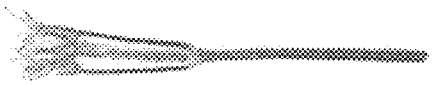

UNITED STATES PATENT AND TRADEMARK OFFICE

CERTIFICATE OF CORRECTION

PATENT NO. : PP 15,165 P2
APPLICATION NO. : 10/640802
DATED : September 21, 2004
INVENTOR(S) : Mogens N. Olesen and Raymond J. Evison It is certified that error appears in the above-identified patent and that said Letters Patent is hereby corrected as shown below:

TITLE PAGE, COLUMN 2

Section 2, line 17 through 25, strike the following text:

"FIG. 1.1 Juvenile stem with petioles and attachment of flower bud;
FIG. 1.2 Mature compound leaf and leaflets;
FIG. 1.3 Flower bud and partially opened flower;
FIG. 1.4 Open flower, upper side;
FIG. 1.5 Open flower, lower side."

Section 2, line 17 insert the following text:

--FIG. 1 Upper and lower surface of open flower with detached tepals;
FIG. 2.1 Flower bud at various stages of opening with peduncle;
FIG. 2.2 Mature stem showing attachment of leaves and leaflets;
FIG. 2.3 Juvenile stem.--

Signed and Sealed this

Sixth Day of March, 2007

JON W. DUDAS
*Director of the United States Patent and Trademark Office*